United States Patent
Olsson et al.

(10) Patent No.: US 6,346,390 B1
(45) Date of Patent: Feb. 12, 2002

(54) RECEPTOR DERIVED PEPTIDES INVOLVED IN MODULATION OF RESPONSE TO LIGAND BINDING

(75) Inventors: Lennart Olsson, Orinda; Tatajna Navrenda, Mountain View, both of CA (US)

(73) Assignee: Receptron, Inc., Mountain View, CA (US)

(*) Notice: Subject to any disclaimer, the term of this patent is extended or adjusted under 35 U.S.C. 154(b) by 0 days.

(21) Appl. No.: 08/788,820

(22) Filed: Jan. 23, 1997

Related U.S. Application Data

(63) Continuation-in-part of application No. 08/701,382, filed on Aug. 22, 1996, now Pat. No. 6,004,758, which is a continuation-in-part of application No. 08/612,999, filed on Mar. 8, 1996, now Pat. No. 5,952,293.

(51) Int. Cl.$^7$ ............................................. G01N 33/566
(52) U.S. Cl. ...................... 435/7.21; 435/7.1; 435/7.8; 435/7.92; 435/7.93; 436/501
(58) Field of Search .................... 436/86, 501; 435/7.1, 435/7.21, 7.8, 7.92, 7.93

(56) References Cited

U.S. PATENT DOCUMENTS 5,385,888 A    1/1995   Goodenow et al.

FOREIGN PATENT DOCUMENTS

| WO | 90-10016 | 9/1990 |
| WO | 95/05189 | 2/1995 |

OTHER PUBLICATIONS

Renfrew Haft et al., "Involvement of Dileucine Motifs in the Internatlization and Degradation of the Insulin Receptor," *Journal of Biological Chemistry*, 289(42)26286–26294 (Oct. 1994).

Hamer, "Dual Role of a Dileucine Motif in Insulin Receptor Endocytosis," *Journal of Biological Chemistry*, 272(35)21685–21691 (Aug. 1997).

Li et al., "An Irregularity in the Transmembrane Domain Helix Correlates with the Rate of Insulin Receptor Internatlization," *Biochemistry*, 33:14333–14338 (1994).

Verhey et al., "Distinct Signals in the GLUT4 Glucose Transporter for Internalization and for Targeting to an Insulin–responsive Compartment," *The Journal of Cell Biology*, 130:1071–1079 (1995).

Hansen et al., "Inhibition of Insulin Receptor, Phosphorylation by Peptides Derived From Major Histocompatibility Complex Class I Antigens," *PNAS USA*, 86:3123–3126 (1989).

Olsson et al., "Regulation of Receptor Internalization by the Major Histocompatibilty Complex Class I Molecule," *PNAS USA*, 91:9086–9090 (1994).

Stagsted et al., "Inhibition of Internatlization of Glucose Transporters and IGF–II Receptors," *The Journal of Biological Chemistry*, 268(30):22809–22813 (1993).

Verland et al., "Specific Molecular Interaction Between the Insulin Receptor and A D Product of MHC Class I," *The Journal of Immunology*, 143(3):945–951 (1989).

Stagsted et al., "Correlation Between Insulin Receptor Occupancy and Tyrosine Kinase Activity at Low Insulin Concentrations and Effect of Major Histocompatibilty Complex Class I–Derived Peptide," *The Journal of Pharmacology and Experimental Therapeutics*, 267(2):997–1001 (1993).

Stagsted et al., "A Preformed, Ordered Structure of a 25–Residue Peptide Derived from a Major Histocompatibility Complex Class I Antiogen Is Required to Affect Insulin Receptor Function," *The Journal of Biological Chemistry*, 266(20): 12844–12847 (1991).

Rajagopalan et al., "Chimeric Receptors Expressing Juxtamembrane Sequences of the Insulin Receptor Undergo Rapid Endocytosis in the Absence of Receptor Tyrosine Kinase Activity," *Biochemical and Biophysical Research Communications*, 211(3):714–718 (1995).

Levy–Toledan et al., "Deletion of C–terminal 113 Amino Acids Impairs Processing and Internalization of Human Insulin Receptor: Comparison of Receptors Expressed in CHO and NIH–3T3 Cells," *Biochimica et Biophysica Acta*, 1220:1–14 (1993).

Staubs et al., "Localization of the Insulin Receptor Binding Sites For the SH2 Domain Proteins p85, Syp, and GAP," *The Journal of Biological Chemistry*, 269(44):27186–27192 (1994).

Stagsted et al., "Regulation of Insulin Receptor Functions by a Peptide Derived from a Major Histocompatibility Complex Class I Antigen," *Cell*, 62:297–307 (1990).

*Primary Examiner*—David Saunders

(57) ABSTRACT

Oligopeptides having an amino acid sequence corresponding to a receptor's extracellular domain, and having sequence similarity to regulatory peptides from MHC class I antigens, enhance the physiological response of ligand binding to the corresponding receptor. The oligopeptides are used in diagnosis and therapy of diseases that involve inadequate or inappropriate receptor response as well as in the screening of drug candidates that affect surface expression of receptors. Also useful for drug screening is a modified receptor molecule, where the sequence corresponding to the regulatory peptide is modified or deleted.

16 Claims, No Drawings

United States Patent

```
                            SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
         (A) LENGTH: 23 amino acids
         (B) TYPE: amino acid
         (C) STRANDEDNESS: unknown
         (D) TOPOLOGY: unknown (ii) MOLECULE TYPE: protein (ix) FEATURE:
         (A) NAME/KEY: CDS
         (B) LOCATION: 50..1030

(xi) SEQUENCE DESCRIPTION: SEQ ID NO:1:

Glu Arg Glu Thr Gln Ile Ala Lys Gly Asn Glu Gln Ser Phe Arg Val
1               5                  10                  15

Asp Leu Arg Thr Leu Leu Arg
            20

(2) INFORMATION FOR SEQ ID NO:2:

(i) SEQUENCE CHARACTERISTICS:
         (A) LENGTH: 23 amino acids
         (B) TYPE: amino acid
         (C) STRANDEDNESS: unknown
         (D) TOPOLOGY: unknown (ii) MOLECULE TYPE: protein (ix) FEATURE:
         (A) NAME/KEY: CDS
         (B) LOCATION: 50..1030

(xi) SEQUENCE DESCRIPTION: SEQ ID NO:2:

Thr Trp Leu Gly Arg Gln Gly Pro Glu Gly Pro Ser Ser Ile Pro Pro
1               5                  10                  15

Gly Thr Leu Thr Thr Leu Trp
            20

(2) INFORMATION FOR SEQ ID NO:3:

(i) SEQUENCE CHARACTERISTICS:
         (A) LENGTH: 24 amino acids
         (B) TYPE: amino acid
         (C) STRANDEDNESS: unknown
         (D) TOPOLOGY: unknown (ii) MOLECULE TYPE: protein (ix) FEATURE:
         (A) NAME/KEY: CDS
         (B) LOCATION: 50..1030

(xi) SEQUENCE DESCRIPTION: SEQ ID NO:3:

Lys Thr Asp Ser Gln Ile Leu Lys Glu Leu Glu Glu Ser Ser Phe Arg
1               5                  10                  15

Lys Thr Phe Glu Asp Tyr Leu His
            20
```

(2) INFORMATION FOR SEQ ID NO:4:

(i) SEQUENCE CHARACTERISTICS:
        (A) LENGTH: 25 amino acids
        (B) TYPE: amino acid
        (C) STRANDEDNESS: unknown
        (D) TOPOLOGY: unknown (ii) MOLECULE TYPE: protein (ix) FEATURE:
        (A) NAME/KEY: CDS
        (B) LOCATION: 50..1030

(xi) SEQUENCE DESCRIPTION: SEQ ID NO:4:

```
Gly Arg Gly Asn Glu Lys Lys Pro Ser Ser Val Arg Ala Leu Ser Ile
1               5                   10                  15

Val Leu Pro Ile Val Leu Leu Val Phe
            20                  25
```

(2) INFORMATION FOR SEQ ID NO:5:

(i) SEQUENCE CHARACTERISTICS:
        (A) LENGTH: 24 amino acids
        (B) TYPE: amino acid
        (C) STRANDEDNESS: unknown
        (D) TOPOLOGY: unknown (ii) MOLECULE TYPE: protein (ix) FEATURE:
        (A) NAME/KEY: CDS
        (B) LOCATION: 50..1030

(xi) SEQUENCE DESCRIPTION: SEQ ID NO:5:

```
Lys Thr Glu Ala Glu Lys Gln Ala Glu Lys Glu Glu Ala Glu Tyr Arg
1               5                   10                  15

Lys Val Phe Glu Asn Phe Leu His
            20
```

(2) INFORMATION FOR SEQ ID NO:6:

(i) SEQUENCE CHARACTERISTICS:
        (A) LENGTH: 23 amino acids
        (B) TYPE: amino acid
        (C) STRANDEDNESS: unknown
        (D) TOPOLOGY: unknown (ii) MOLECULE TYPE: protein (ix) FEATURE:
        (A) NAME/KEY: CDS
        (B) LOCATION: 50..1030

(xi) SEQUENCE DESCRIPTION: SEQ ID NO:6:

```
Lys Lys Glu Asn Lys Ile Val Pro Ser Lys Glu Ile Val Trp Trp Met
1               5                   10                  15

Asn Leu Ala Glu Lys Ile Pro
            20
```

(2) INFORMATION FOR SEQ ID NO:7:

(i) SEQUENCE CHARACTERISTICS:
        (A) LENGTH: 25 amino acids
        (B) TYPE: amino acid
        (C) STRANDEDNESS: unknown
        (D) TOPOLOGY: unknown

```
    (ii) MOLECULE TYPE: protein (ix) FEATURE:
         (A) NAME/KEY: CDS
         (B) LOCATION: 50..1030

(xi) SEQUENCE DESCRIPTION: SEQ ID NO:7:

Glu Lys Lys Pro Val Pro Trp Glu Ser His Asn Ser Ser Glu Thr Cys
1               5                   10                  15

Gly Leu Pro Thr Leu Val Gln Thr Tyr
            20                  25

(2) INFORMATION FOR SEQ ID NO:8:

(i) SEQUENCE CHARACTERISTICS:
        (A) LENGTH: 24 amino acids
        (B) TYPE: amino acid
        (C) STRANDEDNESS: unknown
        (D) TOPOLOGY: unknown (ii) MOLECULE TYPE: protein (ix) FEATURE:
         (A) NAME/KEY: CDS
         (B) LOCATION: 50..1030

(xi) SEQUENCE DESCRIPTION: SEQ ID NO:8:

Tyr Lys Glu Gly Thr Met Leu Asn Cys Glu Cys Lys Thr Gly Phe Arg
1               5                   10                  15

Arg Ile Lys Ser Gly Ser Leu Tyr
            20

(2) INFORMATION FOR SEQ ID NO:9:

(i) SEQUENCE CHARACTERISTICS:
        (A) LENGTH: 24 amino acids
        (B) TYPE: amino acid
        (C) STRANDEDNESS: unknown
        (D) TOPOLOGY: unknown (ii) MOLECULE TYPE: protein (ix) FEATURE:
         (A) NAME/KEY: CDS
         (B) LOCATION: 50..1030

(xi) SEQUENCE DESCRIPTION: SEQ ID NO:9:

Leu Leu Glu Gly Glu Pro Arg Glu Phe Val Glu Asn Ser Glu Cys Ile
1               5                   10                  15

Gln Cys His Pro Glu Cys Leu Pro
            20

(2) INFORMATION FOR SEQ ID NO:10:

(i) SEQUENCE CHARACTERISTICS:
        (A) LENGTH: 27 amino acids
        (B) TYPE: amino acid
        (C) STRANDEDNESS: unknown
        (D) TOPOLOGY: unknown (ii) MOLECULE TYPE: protein (ix) FEATURE:
         (A) NAME/KEY: CDS
         (B) LOCATION: 50..1030

(xi) SEQUENCE DESCRIPTION: SEQ ID NO:10:

Pro Lys Thr Asp Ser Gln Ile Leu Lys Glu Leu Glu Glu Ser Ser Phe
1               5                   10                  15
```

```
Arg Lys Thr Phe Glu Asp Tyr Leu His Asn Val
            20                  25
```

(2) INFORMATION FOR SEQ ID NO:11:

(i) SEQUENCE CHARACTERISTICS:
        (A) LENGTH: 36 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:11:

```
Gly Asn Glu Gln Ser Phe Arg Val Asp Leu Arg Thr Leu Leu Arg Tyr
1               5                   10                  15

Ala Gly Gly Asn Glu Gln Ser Phe Arg Val Asp Leu Arg Thr Leu
            20                  25                  30

Leu Arg Tyr Ala
            35
```

(2) INFORMATION FOR SEQ ID NO:12:

(i) SEQUENCE CHARACTERISTICS:
        (A) LENGTH: 28 amino acids
        (B) TYPE: amino acid
        (C) STRANDEDNESS: unknown
        (D) TOPOLOGY: unknown (ii) MOLECULE TYPE: protein (ix) FEATURE:
        (A) NAME/KEY: CDS
        (B) LOCATION: 50..1030

(xi) SEQUENCE DESCRIPTION: SEQ ID NO:12:

```
Glu Tyr Glu Leu Gln Tyr Lys Glu Val Asn Glu Thr Lys Trp Lys Met
1               5                   10                  15

Met Asp Pro Ile Leu Thr Thr Ser Val Pro Val Tyr
            20                  25
```

US 6,346,390 B1

RECEPTOR DERIVED PEPTIDES INVOLVED IN MODULATION OF RESPONSE TO LIGAND BINDING

CROSS-REFERENCE TO RELATED APPLICATIONS

This application is a continuation-in-part of application Ser. No. 08/701,382, filed Aug. 22, 1996 and now U.S. Pat. No. 6,004,758, which is a continuation-in-part of application Ser. No. 08/612,999, filed Mar. 8, 1996 and now U.S. Pat. No. 5,952,293.

INTRODUCTION

Technical Field

The field of this invention is the modulation of response to ligands by cell surface receptors.

Background

The complex regulatory balance between hormones, receptors and responding cells is critical to the correct functioning of multicellular organisms. Subtle environmental and genetic factors can disrupt this balance, sometimes resulting in disease. The advent of molecular biology has meant that medically important hormones can be made available in therapeutically useful amounts. Among them are human growth hormone, insulin-like growth factor, insulin, epidermal growth factor, and numerous others.

A condition of great economic and medical significance is insulin resistance, which is an essential feature of a great variety of clinical disorders, such as diabetes mellitus, obesity and certain types of hypertension. Individuals with non-insulin dependent diabetes present with insulin resistance in peripheral tissues. They have a subnormal glucose utilization in skeletal muscle, where glucose transport across the cell membrane of skeletal muscle is the rate limiting step in glucose metabolism. It is possible that a defect exists in insulin-dependent glucose transport in skeletal muscle in diabetic states, where decreased levels of the glucose transporter 4 protein (GLUT4) have been observed. In adipose and muscle cells, insulin stimulates a rapid and dramatic increase in glucose uptake, primarily by promoting the redistribution of the GLUT4 glucose transporter from its intracellular storage site to the plasma membrane.

Insulin resistance may also be attributed to a defect in insulin action at the cellular level. The insulin receptor is activated by binding of insulin to the alpha-subunit of the receptor, which causes autophosphorylation of the intracellular beta-subunit region. The activated insulin receptor couples to cytosolic receptor substrates that can affect signaling cascades, resulting in the pleiotropic hormone response. Most proteins involved in the signal transduction pathway are not known yet, but each of them might play a role in the various forms of insulin resistance. The heterogeneous nature of insulin resistance makes treatments that can act "upstream" of the signal transduction pathways very attractive, because a number of different pathologies could be treated with a single drug.

Specific peptides have been previously shown to enhance the cellular response to certain hormones. This effect has been attributed to inhibition of the internalization of the corresponding hormone receptors. Insulin-stimulated glucose uptake is increased by adding the peptides to responding cells, offering the possibility of improved therapy for insulin dependent and insulin resistant diabetes. The enhanced response may also be exploited in therapies involving other hormones. Improvements in the specificity of agents that enhance the activity of insulin and other hormones are of considerable interest for their therapeutic benefits. The site of action for such peptides on receptors molecules is of interest for drug evaluation and design.

Relevant Literature

Several groups have examined the glucose transporter and insulin receptor for residues that are involved in internalization. Rajagopalan et al. (1995) *Biochem. Biophys. Res. Commun.* 211:714–8 found that residues GPYL950–953 served as the predominant endocytosis signal and the sequence NPEY957–960 as a secondary signal. Levy-Toledano et al. (1993) *Biochem. Biophys. Acta.* 1220:1–14 suggest that the structural domain located 43–113 amino acids from the C-terminus is required in intact cells for insulin-stimulated autophosphorylation and signal transmission. Verhey et al. (1995) *J. Cell Biol.* 130:1071–9 identified sequences involved in the differential subcellular localization and hormone-responsiveness of glucose transporter isoforms. The COOH-terminal 30 amino acids of GLUT4 are sufficient for its correct localization to an intracellular storage pool that translocates to the cell surface in response to insulin.

U.S. Pat. No. 5,385,888, issued Jan. 31, 1995, describes Class I MHC peptide modulation of surface receptor activity. Data presented in International patent application PCT/US94/09189 suggest that these peptides must be in an ordered conformation to be biologically active. The composition and uses of such peptides are further described in International application PCT/US93/01758. The peptides are further disclosed in International application PCTIUS89/00876.

Regulation of receptor internalization by the major histocompatibility complex class I molecule is shown by Olsson et al. (1994) *Proc. Natl. Acad. Sci.* 91:9086–90. Peptides derived from the alpha 1 domain of the major histocompatibility complex class I protein (MHC-I) inhibit internalization of some receptors, thereby increasing the steady-state number of active receptors on the cell surface. It is suggested that MHC-I participates in the regulation of cell surface receptor activity. Stagsted et al. (1993) *J. Biol. Chem.* 268:22809–13 demonstrate that such peptides inhibit the internalization of glucose transporters (GLUT4) and insulin-like growth factor II (IGF-II) receptors in insulin-stimulated cells.

SUMMARY OF THE INVENTION

Methods and compositions are provided for determining, in a cell surface receptor protein, an extracytoplasmic region that is involved with internalization. Identification of the amino acid sequence in this region permits the design of drug screening assays for bioactive compounds that modulate receptor internalization. Oligopeptides, having at least substantially the amino acid sequence of that portion of that receptor's extracellular domain, modulate the response of cell surface receptors to ligand binding.

The receptor derived peptides have sequence similarity to previously described regulatory peptides from the major histocompatibility complex class I antigens. The methods and compositions of the subject invention are used in diagnosis and therapy of diseases that involve inadequate or inappropriate receptor response as well as in the screening of drug candidates that affect surface expression of receptors. Also useful for drug screening is a modified receptor molecule, where the sequence corresponding to the regulatory peptide is modified or deleted.

DATABASE REFERENCES FOR NUCLEOTIDE AND AMINO ACID SEQUENCES

The complete mRNA sequence encoding the human insulin responsive glucose transporter (GLUT4) has the Genbank accession number M20747, published by Fukumoto et al. (1989) *J. Biol. Chem.* 264:7776–7779. The complete mRNA sequence encoding the human insulin receptor has the Genbank accession number A18657, published in International Patent Application No. WO/91/17253. The complete mRNA sequence encoding the human leptin receptor has the Genbank accession number U43168, and was published by Tartaglia et al. (1995) *Cell* 83:1263–1271. The DNA sequence encoding the human granulocyte colony stimulating factor (G-CSF) receptor has the EMBL accession numbers M59820, M38027, X55720 and X55721, and was published by Larsen et al. (1990) *J. Exp. Med.* 172:1559–1570. The complete sequence of the human interleukin 2 (IL-2) receptor has the Swissprot accession number P01589, and was published by Leonard et al. (1984) *Nature* 311:626–631. The complete sequence of the human epidermal growth factor (EGF) receptor has the Swissprot accession number P00533, and was published by Ullrich et al. (1984) *Nature* 309:418–425. The sequences for other cell surface receptors are known, and easily ascertainable by those in the art.

The sequences of known HLA and H-2 alleles may be found in Kabat et al. (1991) *Sequences of Proteins of Immunological Interest*, N.I.H. publication no. 91–3242, vol. 1, pp. 738–740, 761, 770–771, 779–780, 788–789 and 802–804.

DESCRIPTION OF THE SPECIFIC EMBODIMENTS

The present invention is based on the discovery that sequences on the extracellular portion of cell surface receptors, "internalization sequences", bind to each other to prevent internalization of the receptors. Fortuitously, the internalization sequences are not directly involved in ligand binding. The effective dimerization or oligomerization of the internalization sequences thus allows for the design of oligopeptides which mimic these sequences. Thus, oligopeptides which mimic these sequences are useful to inhibit the internalization of the receptors, thereby providing for a greater number of receptors on the cell surface. This increase or stabilization of the number of receptors at the cell surface can result in increased effectiveness of ligand binding. This has therapeutic relevance in a number of disease conditions where decreased ligand binding or signalling is a problem. For example, there are a number of diseases where hormone sensitivity is reduced or the production of the hormone is decreased, such that increased efficiency of ligand signalling is desirable. For example, non-insulin dependent diabetes mellitus (NIDDM) is such a condition.

Cell surface receptors of interest are internalized or are recycled into the cytoplasm in response to ligand binding. Generally, a regulatory peptide will be derived from the sequence of the receptor that is to be modulated. The sequence of interest corresponds to the region of the receptor on the extracellular surface, but usually is not directly involved in ligand binding, i.e. contact is not made with the ligand. Sequences of receptors, and positioning of the receptors in the cell membrane are known in the art. Such information may be accessed through public databases, as previously cited.

Accordingly, the present invention provides regulatory oligopeptides comprising internalization sequences that have an amino acid sequence at least substantially identical to the sequence of a portion of a cell surface receptor extracellular domain. Generally, these oligopeptides also have sequence similarity to bioactive oligopeptides of the major histocompatibility locus class I antigens (described in U.S. Pat. No. 5,385,888, herein incorporated by reference). The oligopeptides modulate the effect of ligand binding to the corresponding receptor, thereby enhancing the physiological effect of the ligand.

The internalization sequences are initially identified by homology to the sequence of an $\alpha_1$-domain of an MHC Class I antigen. MHC Class I antigens include human MHC Class I antigens and mammalian equivalents thereof, such as Class I antigens of the H-2 locus of mice, in particular H-2 D and K. Human MHC Class I antigens include HLA-A, B and C. Of more particular interest are the amino acid sequences in the polymorphic regions of the α-1 domain, more particularly amino acids 55 to 90, usually 60 to 90, more particularly 62 to 90. The region 60–85 of the α-1 domain, more particularly 62–85 or 72–82 are found to be of particular interest. One MHC sequence of particular interest is ERETQIAKGNEQSFRVDLRTLLR, (SEQ ID NO: 1; U.S. Pat. No. 5,385,888). Thus, oligopeptides with sequence similarity to these regions are preferred.

Using these sequences, and in particular SEQ ID NO: 1, the sequences of any number of cell surface receptors are scanned for homologous regions. Suitable cell surface receptors include, but are not limited to, insulin receptor, insulin-like growth factor receptor, human growth hormone receptor, glucose transporters, transferrin receptor, epidermal growth factor receptor, low density lipoprotein receptor, epidermal growth factor receptor, leptin receptor, interleukin receptors, e.g. IL-1 receptor, IL-2 receptor, etc. Algorithms for sequence analysis are known in the art, and include BLAST, described in Altschul et al. (1990) *J. Mol. Biol.* 215:403–10; ADVANCE and ADAM, described in Torelli and Robotti (1994) *Comput. Appl. Biosci.* 10:3–5; and FASTA, described in Pearson and Lipman (1988) *P.N.A.S.* 85:2444–8. The sequence similarity may be determined using the Wisconsin Package, version 8.0-Open VMS, Genetics Computer Group.

Preferably, the amino acid sequence of the receptor region of interest will have at least about 10% sequence identity, and frequently at least about 20% sequence identity. The sequence similarity will be at least about 35%, and frequently at least about 45%. The examples provide the results of exemplary similarity searches.

Exemplary receptor derived amino acid sequences of interest include (SEQ ID NO:2) TWLGRQGPEGPSSIPPGTLTTLW (human glucose transporter, GLUT4); (SEQ ID No:3) KTDSQILKELEESSFRKTFEDYLH (human insulin receptor); (SEQ ID No:4) GRGNEKKPSSVRALSIVLPIVLLVF (human LDL receptor); (SEQ ID No:5) KTEAEKQAEKEEAEYRKVFENFLH (human insulin like growth factor receptor); (SEQ ID NO:6) KKENKIVPSKEIVWWMNLAEKIP (human leptin receptor); (SEQ ID NO:7) EKKPVPWESHNSSETCGLPTLVQTY (human GCSF receptor); (SEQ ID NO:8) YKEGTMLNCECKTGFRRIKSGSLY (human interleukin 2 receptor); (SEQ ID NO: 9) LLEGEPREFVENSECIQCHPECLP (human epidermal growth factor receptor), and (SEQ ID NO:12) EYELQYKEVNETKWKMMDPILTTSVPVY) (human growth factor receptor).

The receptor sequence of interest, ie. the internalization sequence, will comprise, as an active motif sequence, at least 8 amino acids, usually at least about 12 amino acids, more usually at least about 18 amino acids, and fewer than about 40 amino acids, more usually fewer than 30 amino acids.

As will be appreciated by those in the art, the internalization sequences may be modified, either as modified oligopeptides or as modified receptors, where the receptors are made with modified internalization sequences.

In a preferred embodiment, the internalization sequences of the regulatory oligopeptides are altered. Preferably, any modifications do not substantially alter the biological activity, i.e. inhibition of internalization or aggregation, of the internalization sequence for the corresponding receptor. This is easily tested using the binding assays described herein. For example, amino acid substitutions, insertions and deletions may be made.

In one embodiment, amino acid substitutions are made. In general, it is preferable that residues critical for biological activity are either not altered or conservatively altered. Critical residues may be elucidated using known mutagenesis techniques followed by activity or binding assays; for example, using scanning mutagenesis techniques, wherein single amino acid residues within the internalization sequence are modified by substitution with an aliphatic amino acid, e.g. serine, alanine, glycine, valine, etc. It is also preferred that not more than about three substitutions or deletions will be made, and that the change will not be more than about 20 number %, usually not more than about 10 number %, of the number of amino acids in the active motif. However, if only non-critical residues are altered, this may be higher. Preferred are conservative substitutions, as known in the art, including substitutions within the large hydrophobic group: isoleucine, leucine, valine and phenylalanine; between serine and threonine; glycine and alanine; asparagine and glutamine; aspartic acid and glutamic acid; or lysine, arginine and histidine. In some embodiments, non-conservative alterations are done.

In addition to modifications within the internalization sequences, the oligopeptides may contain additional sequences, as will be appreciated by those in the art. For example, the oligopeptides may be extended to: 1) provide convenient linking sites, e.g. cysteine or lysine; 2) to enhance stability; 3) to bind to particular receptors; 4) to provide for site-directed action; 5) to provide for ease of purification (for example, epitope or purification ($His_6$) tags); 6) to alter the physical characteristics (e.g. solubility, charge, etc.); or 7) to stabilize the conformation; etc. The oligopeptides may be joined to non-wild-type flanking regions as fused proteins, joined either by linking groups or covalently linked through cysteine (disulfide) or peptide linkages.

The oligopeptide may be linked through a variety of bifunctional agents, such as maleimidobenzoic acid, methyidithioacetic acid, mercaptobenzoic acid, S-pyridyl dithiopropionate, etc. The oligopeptides may be joined to a single amino acid at the N- or C-terminus of a chain of amino acids, or may be internally joined. For example, the subject peptides may be covalently linked to an immunogenic protein, such as keyhole limpet hemocyanin, ovalbumin, etc. to facilitate antibody production to the subject oligopeptides.

Alternatively, the subject oligopeptides may be expressed in conjunction with other peptides or proteins, so as to be a portion of the chain, either internal, or at the N- or C-terminus. Various post-expression modifications may be achieved. For example, by employing the appropriate coding sequences, one may provide farnesylation or prenylation, such that the subject peptide will be bound to a lipid group at one terminus, and will be able to be inserted into a lipid membrane, such as a liposome.

The subject oligopeptides may be PEGylated, where the polyethyleneoxy group provides for enhanced lifetime in the blood stream. The subject oligopeptides may also be combined with other proteins, such as the Fc of an IgG isotype to enhance complement binding, or with a toxin, such as ricin, abrin, diphtheria toxin, or the like, particularly the A chain. The oligopeptides may be linked to antibodies for site directed action. For conjugation techniques, see, for example, U.S. Pat. Nos. 3,817,837; 3,853,914; 3,850,752; 3,905,654; 4,156,081; 4,069,105; and 4,043,989, which are incorporated herein by reference.

Oligomers of the regulatory oligopeptides of the invention may also be made. For example, oligopeptides of interest for drug screening include, but are not limited to: 1) an oligopeptide having at least substantially the sequence of the receptor region of interest; 2) MHC/receptor oligopeptide heterodimers having the sequence of the receptor region of interest and the amino acid sequence of bioactive oligopeptides of the major histocompatibility locus class I antigens; and 3) receptor derived oligopeptide homodimers, generally as a head to tail dimer, where a spacer of from 1 to 3 small neutral amino acids may be present between the two active peptide sequences.

Once identified, the oligopeptides comprising the internalization sequences may be prepared in accordance with conventional techniques, such as synthesis (for example, use of a Beckman Model 990 peptide synthesizer or other commercial synthesizer). Peptides may be produced directly by recombinant methods (see Sambrook et al. *Molecular Cloning: A Laboratory Manual*, CSHL Press, Cold Spring Harbor, N.Y., 1989) or as a fusion protein, for example to a protein that is one of a specific binding pair, allowing purification of the fusion protein by means of affinity reagents, followed by proteolytic cleavage, usually at a site engineered to yield the desired peptide (see for example Driscoll et al. (1993) *J. Mol. Bio.* 232:342–350).

In a preferred embodiment, the internalization sequence contained within the receptor is altered, to form a modified receptor. In a modified form of the receptor, the sequence corresponding to the regulatory peptide (i.e. the internalization sequence) contains an insertion, substitution or deletion, such that the ability of the receptor to internalize in response to ligand binding is altered. The modification may include a deletion or substitution of the complete oligopeptide sequence, or a portion thereof. Substitutions of interest also include scanning mutations as outlined above.

Conveniently, the modification is performed using recombinant DNA technology. The DNA sequence encoding the desired receptor may be obtained from various sources, or may be obtained from a cDNA library using probes derived from publically available sequence information. Techniques for in vitro mutagenesis of cloned genes are known; methods for site specific mutagenesis can be found in Sambrook, et al. supra. pp 15.3–15.108; Weiner et al. (1993) *Gene* 126:3541; Sayers et al. (1992) *Biotechniques* 13:592–6; Jones and Winistorfer (1992) *Biotechniques* 12:528–30; Barton et al. (1990) *Nucleic Acids Res.* 18:7349–55; Marotti and Tomich (1989) *Gene Anal. Tech.* 6:67–70 and Zhu (1989) *Anal. Biochem.* 177:1204. For example, to delete a sequence, primers are devised that span the region. On hybridization, the region to be deleted forms a single stranded loop. The loop may be excised by nuclease digestion, or a suitable polymerase may be used to extend out from the primer.

For expression, the DNA sequences are inserted into an appropriate expression vector, where the native transcriptional initiation region may be employed or an exogenous transcriptional initiation region, i.e., a promoter other than the promoter which is associated with the gene in the normally occurring chromosome. The promoter may be introduced by recombinant methods in vitro, or as the result of homologous integration of the sequence into a chromosome. A wide variety of transcriptional initiation regions are known for a wide variety of expression hosts. Generally a selectable marker operative in the expression host will be present. The promoter may be operably linked to the coding sequence of the genes of interest so as to produce a translatable mRNA transcript. Expression vectors have convenient restriction sites located near the promoter sequence so as to provide for the insertion of nucleic acid sequences encoding heterologous proteins. The promoters in suitable expression vectors may be either constitutive or inducible. Expression vectors for the production of fusion proteins, where the exogenous fusion peptide provides additional functionality, i.e. increased protein synthesis, stability, reactivity with defined antisera, an enzyme marker, e.g., b-galactosidase, etc.

The expression vectors are transformed into a host cell. The expression hosts may involve prokaryotes or eukaryotes, particularly *E. coli; B. sublilis*; yeast cells; mammalian cells; e.g., COS and CHO cells, HeLa cells, L(tk-), primary cultures; insect cells; *Xenopus laevis* oocytes; and the like. Particularly preferred host cells are mammalian cells.

Once made, the oligopeptides and modified receptors find use in a number of applications.

In a preferred embodiment, the oligopeptides are used in methods for inhibiting the internalization of a cell surface receptor response of a mammalian cell. The methods comprises adding oligopeptides as defined herein to mammalian cells expressing the cell surface receptor. Upon addition (either simultaneous or sequential) of the ligand which binds the receptor, the oligopeptide inhibits the receptor internalization.

Accordingly, in a preferred embodiment, the oligopeptides are administered therapeutically. The subject oligopeptides act to enhance the cellular response to hormones that bind to the surface membrane receptor corresponding to the oligopeptide, e.g. insulin response is enhanced by the oligopeptide SEQ ID No:3, glucose transport is enhanced by the oligopeptide SEQ ID No:2, etc. Hormones including insulin, insulin-like growth factor, human growth hormone, glucose transporters, transferrin, epidermal growth factor, low density lipoprotein, human growth hormone and epidermal growth factor are herein referred to as "therapeutic hormones". Enhancement of the cellular response to therapeutic hormones by the subject oligopeptides provides a means of improving the response of patients that are unresponsive, e.g. resistant, to the action of such hormones. The subject oligopeptides may be administered to patients requiring enhancement of the response to naturally occurring levels of the therapeutic hormone. Alternatively, the oligopeptides may be administered to patients in conjunction with a therapeutic hormone. Of particular interest is the treatment of insulin resistance, which may be associated with defects in glucose transport, or in the cellular response to insulin. Administration of the subject oligopeptides improves the response to insulin therapy. Similarly, enhancement of the effect of human growth hormone is also of particular interest. Human growth hormone is current given in a number of clinical situations as an injectible drug; alternative therapies may include augmenting the response of endogeneous hormone.

For therapy, the oligopeptides may be administered topically or parenterally, e.g. by injection at a particular site, for example, subcutaneously, intraperitoneally, intravascularly, intranasally, transdermally or the like. Formulations for injection will comprise a physiologically-acceptable medium, such as water, saline, PBS, aqueous ethanol, aqueous ethylene glycols, or the like. Water soluble preservatives which may be employed include sodium bisulfite, sodium thiosulfate, ascorbate, benzalkonium chloride, chlorobutanol, thimerosal, phenylmercuric borate, parabens, benzyl alcohol and phenylethanol. These agents may be present in individual amounts of from about 0.001 to about 5% by weight and preferably about 0.01 to about 2%. Suitable water soluble buffering agents that may be employed are alkali or alkaline earth carbonates, phosphates, bicarbonates, citrates, borates, acetates, succinates and the like, such as sodium phosphate, citrate, borate, acetate, bicarbonate and carbonate. Additives such as carboxymethylcellulose may be used as a carrier in amounts of from about 0.01 to about 5% by weight. The formulation will vary depending upon the purpose of the formulation, the particular mode employed for modulating the receptor activity, the intended treatment, and the like. The formulation may involve patches, capsules, liposomes, time delayed coatings, pills, or may be formulated in pumps for continuous administration. The specific dosage can be determined empirically in accordance with known ways. See, for example Harrison's, Principles of Internal Medicine, 11th ed. Braunwald et al. ed, McGraw Hill Book Co., New York, 1987.

Generally, a therapeutically effective dose of the subject oligopeptides will be in the range of about 0.005–10, more usually from about 0.01–1 mg/kg of host weight. Such a dose will be sufficient to enhance the action of the therapeutic hormone, usually by at least as much as 50%. Administration may be as often as daily; usually not more than one or more times daily, or as infrequent as weekly, depending upon the level of drug which is administered. The oligopeptides may be administered alone, or in combination with the therapeutic hormone. The hormone may be administered at a normally therapeutically effective dose, or the dose may be decreased by as much as 50%, usually by as much as 25%, to compensate for the oligopeptide enhancement. The host may be any mammal including domestic animals, pets, laboratory animals and primates, particularly humans. The amount will generally be adjusted depending upon the half life of the peptide, where dosages in the lower portion of the range may be employed where the peptide has an enhanced half life or is provided as a depot, such as a slow release composition comprising particles, introduced in a matrix which maintains the peptide over an extended period of time, e.g., a collagen matrix, use of a pump which continuously infises the peptide over an extended period of time over a substantially continuous rate, or the like. Heller, *Biodegradable Polymers in Controlled Drug Delivery*, in: CRC Critical Reviews in Therapeutic Drua Carrier Systems, Vol. 1, CRC Press, Boca Raton, Fla., 1987, pp 39–90, describes encapsulation for controlled drug delivery, and Di Colo (1992) *Biomaterials* 13:850–856 describes controlled drug release from hydrophobic polymers.

In a preferred embodiment, the oligopeptides, modified receptors and cells containing the modified receptors are used in screening assays. Identification of the amino acid sequence in this region of receptors permits the design of drug screening assays for compounds that modulate receptor internalization.

Drug screening assays utilize the subject sequence information and peptide compositions, e.g., proteins, oligopeptides and synthetic derivatives thereof, to identify agents that modulate the internalization of cell surface receptors. Drug candidates capable of modulating surface receptor internalization are identified by first screening the drug candidates for the ability to compete with a bioactive oligopeptide for association with the intact receptor or that interfere with the binding of an oligopeptide to the subject receptor derived oligopeptides.

Thus, in a preferred embodiment, the methods comprise combining a cell surface receptor which contains an internalization sequence and a candidate bioactive agent, and determining the binding of the candidate agent to the internalization sequence. By "cell surface receptor" herein is meant any of number of cell surface receptors which are usually internalized upon ligand binding. Suitable cell surface receptors include, but are not limited to, insulin receptor, glucose transporter receptor, LDL receptor, insulin-like growth factor receptor, leptin receptor, GCSF receptor, interleukin receptors including IL-2 receptor, epidermal growth factor receptor, and growth hormone receptor. Preferred embodiments utilize the human cell surface receptors, although other mammalian receptors may also be used, including mice, rats and primates. Included within the definition of cell surface receptors are amino acid substitions, insertions, or deletions of the naturally occuring sequence. Preferably, these do not alter the biological activity of the receptors, although as outlined herein, in some instances it may be desirable to modify the biological activity of the receptors.

Furthermore, included within the definition of cell surface receptors are portions of cell surface receptors; that is, either the full-length receptor may be used, or functional portions thereof. In a preferred embodiment, the funtional domain comprises at least a ligand binding domain and an internalization sequence, such that the conformational change that occurs upon ligand binding to the receptor will still occur.

Generally, in a preferred embodiment of the methods herein, the cell surface receptor is non-diffusably bound to an insoluble support having isolated sample receiving areas (e.g. a microtiter plate, an array, etc.). The insoluble supports may be made of any composition to which peptide, or receptor can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose. Microtiter plates and arrays are especially convenient because a large number of assays can be carried out simultaneously, using small amounts of reagents and samples. The particular manner of binding of the peptide or other protein is not crucial so long as it is compatible with the reagents and overall methods of the invention, maintains the activity of the peptide and is nondifflusable. Preferred methods of binding include the use of antibodies (which do not sterically block either the ligand binding site or internalization sequence when the receptor is bound to the support), direct binding to "sticky" or ionic supports, chemical crosslinking, etc. Following binding of the peptide or receptor, excess unbound material is removed by washing. The sample receiving areas may then be blocked through incubation with bovine serum albumin (BSA), casein or other innocuous protein.

In a preferred embodiment, a ligand or analog bound by the cell surface receptor will also be added to the assay. That is, when insulin receptors are used, the ligand is insulin; when human growth hormone receptors are used, the ligand is human growth hormone; etc. As will be appreciated by those in the art, ligand analogs may also be used.

A candidate bioactive agent is added to the assay. Novel binding agents include specific antibodies, non-natural binding agents identified in screens of chemical libraries, peptide analogs, etc., of particular interest are screening assays for agents that have a low toxicity for human cells. A wide variety of assays may be used for this purpose, including labeled in vitro protein-protein binding assays, electrophoretic mobility shift assays, immunoassays for protein binding, and the like.

The term "agent" as used herein describes any molecule, e.g., protein, oligopeptide, small organic molecule, polysaccharide, polynucleotide, etc., with the capability of directly or indirectly altering cell surface receptor internalization in response to ligand binding. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

The determination of the binding of the candidate bioactive agent to the receptor may be done in a number of ways. In one embodiment, the candidate bioactive agent is labelled, and binding determined directly.

By "labeled" herein is meant that the compound is either directly or indirectly labeled with a label which provides a detectable signal, e.g. radioisotope, fluorescers, enzyme, antibodies, particles such as magnetic particles, chemiluminescer, etc.

Where the screening assay is a binding assay, one or more of the molecules may be joined to a label, where the label can directly or indirectly provide a detectable signal. Various labels include radioisotopes, fluorescers, chemiluminescers, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule which provides for detection, in accordance with known procedures. In some embodiments, only one of the components is labeled. For example, the oligopeptides may be labeled at tyrosine positions using $^{125}$I (for example, the internalization sequences of the human GLUT4, insulin, IGF-1, G-CSF, IL-2 and hGH receptors all contain tyrosine residues). Alternatively, more than one component may be labeled with different labels; using $^{125}$I for the oligopeptides, for example, and a fluorophor for the candidate agents.

In a preferred embodiment, the binding of the candidate bioactive agent is determined through the use of competitive binding assays. In this embodiment, the competitor is an oligopeptide as described herein.

In one embodiment, the candidate bioactive agent is labeled. Either the candidate bioactive agent, or the oligopeptide, is added first to the receptor for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the oligopeptide is added first, followed by the candidate bioactive agent. Displacement of the oligopeptide is an indication that the candidate bioactive agent is binding to the internalization sequence and thus is capable of modulating the internalization of the receptor. In this embodiment, either component can be labeled. Thus, for example, if the oligopeptide is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the oligopeptide. The absence of binding by the oligopeptide may indicate that the bioactive agent is bound to the receptor with a higher affinity. Thus, if the candidate bioactive agent is labeled, the presence of the label on the support, coupled with a lack of oligopeptide binding, may indicate that the candidate agent is capable of binding to the internalization sequence and modulating the internalization of the receptor.

In a preferred embodiment, the methods comprise combining a cell surface receptor, a ligand bound by the receptor, and an oligopeptide as described herein, to form a test mixture. The candidate bioactive agent is added to the test mixture, and the binding of the candidate bioactive agent to the internalization sequence of the receptor is determined. In this embodiment, either or both of the oligopeptide or the candidate bioactive agent is labeled, with preferred embodiments utilizing labeled oligopeptides, such that displacement of the label indicates binding by the candidate bioactive agent.

In a preferred embodiment, the methods comprise differential screening to identify bioactive agents that are capable of modulating the internalization of receptors. In this embodiment, the methods comprise combining a cell surface receptor, a ligand, and an oligopeptide in a first sample. A second sample comprises a candidate bioactive agent, a cell surface receptor, a ligand, and an oligopeptide. The binding of the oligopeptide is determined for both samples, and a change, or difference in binding between the two samples indicates the presence of an agent capable of modulating the internalization of the receptor. That is, if the binding of the oligopeptide is different in the second sample relative to the first sample, the agent is capable of binding the internalization sequence.

Alternatively, a preferred embodiment utilizes differential screening to identify drug candidates that bind to the native receptor, but cannot bind to modified receptors, for example those that have the internalization sequences deleted. The structure of the receptor sequence of interest may be modeled, and used in rational drug design to synthesize agents that interact with that site. Drug candidates that affect receptor internalization are also identified by screening drugs for the ability to either enhance or reduce the effect of the subject receptor derived oligopeptides on the internalization of a selected surface receptor.

Screening may be performed to find agents that interfere with the association of a bioactive MHC-derived oligopeptide with the subject oligopeptides, where the agents will be capable of modulating the internalization the receptors from which the subject oligopeptides are derived. This is done using the methods described above, but replacing the oligopeptides with a sequence from a α1-domain of an MHC Class I antigen, such as SEQ ID NO: 1.

The drug candidate and varying concentrations of the subject receptor-derived oligopeptides are added to each of the sample receiving areas containing support-bound peptide. The oligopeptide added is of substantially the same amino acid sequence as the oligopeptide bound to the support and is labeled.

Positive controls for binding of active peptide and competitive binding of active peptide may include samples containing labeled active peptide alone and a mixture of labeled active peptide and unlabeled active peptide, respectively. Samples containing labeled active peptide and unlabeled inactive peptide that does not aggregate with the bound peptide may serve as a negative control for competitive binding with peptide. Preferably all control and test samples are performed in at least triplicate to obtain statistically significant results. Incubation of all samples is for a time sufficient for the binding of the labeled active peptide to the support-bound peptide. Following incubation, all samples are washed free of non-specifically bound material and the amount of bound, labeled peptide determined. For example, where a radiolabel is employed in labeling the peptide, the samples may be counted in a scintillation counter to determine the amount of bound, labeled peptide.

In test samples containing the drug candidate, if the amount of labeled active peptide bound to the support-bound peptide or receptor is in the range of values of the positive control samples for competitive binding and is significantly less than the negative control samples for competitive binding, then the drug candidate in the test sample is able to successfully competitively bind the support-bound peptide. Drug candidates capable of such competitive binding may mediate modulation of cell surface expression of a receptor.

A variety of other reagents may be included in the screening assay. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease innlbitors, anti-microbial agents, etc., may be used.

The mixture of components may be added in any order that provides for the requisite binding.

Compounds with pharmacological activity are able to enhance or interfere with the internalization of cell surface receptors in response to ligand binding. Binding to the site on the receptor corresponding to the subject oligopeptides is indicative of such activity, as is the ability to interfere with the binding of the subject oligopeptides to the cognate receptor. The compounds having the desired pharmacological activity may be administered in a physiologically acceptable carrier to a host, as previously described. The inhibitory agents may be administered in a variety of ways, orally, parenterally e.g., subcutaneously, intraperitoneally, intravascularly, etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Accordingly, methods are provided for enhancing the physiological effect of ligand binding to cell surface receptors by administration of such bioactive, receptor derived oligopeptides, oligopeptide homodimers, and MHC/receptor oligopeptide heterodimers. The methods are used in diagnosis and therapy of diseases that involve inadequate or inappropriate receptor response. The data indicate that internalization of the receptor is inhibited by the presence of the subject oligopeptides, thereby providing for a greater number of receptors on the cell surface, and increased effectiveness of ligand binding.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXPERIMENTAL

Example 1

In order to determine the region on the external domain of a cell surface receptor that is involved in receptor internalization, a sequence similarity comparison was performed. The comparisons were performed with the commercially available Wisconsin Package, version 8.0-open VMS, Genetics Computer Group. The complete receptor sequences were obtained from public databases, as previously described in the "Database References for Nucleotide and Amino Acid Sequences".

The similarity is based on the evolutionary distance between amino acids, as measured by Dayhoff and normalized by Gribskov and Burgess (1986) *Nucl. Acids Res.* 14:6745–6763. The "local homology" algorithm of Smith and Waterman (1981) *Advances in Applied Mathematics* 2:482–289 finds the best segments of similarity between the two sequences.

A similarity search between SEQ ID No: 1 and amino acid sequences of the cell surface receptors: human GLUT4 transporter, human insulin receptor, human LDL receptor, human IGF-1 receptor, human IL-2 receptor, human leptin (OB) receptor, human G-CSF receptor, human insulin-like growth factor receptor and human epidermal growth factor receptor determined that the receptor region sequences SEQ ID No:2 through SEQ ID No:9 had the highest degree of similarity to the MHC bioactive peptide sequence.

TABLE 1

<table>
<tr><th colspan="2">Sequence similarities</th></tr>
<tr><td>ERETQIAKGNEQSFRVDLRTLLR</td><td>MHC; SEQ ID NO:1</td></tr>
<tr><td>.: .. :.:.. |:..: | |:</td><td>39% similar</td></tr>
<tr><td>TWLGRQGPEGPSSIPPGTLTTLW</td><td>GLUT4 transporter; SEQ ID NO:2</td></tr>
<tr><td>ERETQIAKG NEQSFRVDLRTLLR</td><td>MHC; SEQ ID NO:1</td></tr>
<tr><td>. :.|| |: :| ||| .: ..|:</td><td>56% similar</td></tr>
<tr><td>KTDSQILKELEESSFRKTFEDYLH</td><td>Insulin receptor; SEQ ID NO:3</td></tr>
<tr><td>ERETQIAKGNEQSFRVDLRTLLRRY</td><td>MHC; SEQ ID NO:1</td></tr>
<tr><td>:|:.: .:. ..:.: |..:| :</td><td>44% similar</td></tr>
<tr><td>GRGNEKKPSSVRALSIVLPIVLLVF</td><td>LDL receptor; SEQ ID NO:4</td></tr>
<tr><td>ERETQIAKG NEQSFRVDLRTLLR</td><td>MHC; SEQ ID NO:1</td></tr>
<tr><td>. | : : : | : .:|:</td><td>50% similar</td></tr>
<tr><td>KTEAEKQAEKEEAEYRKVFENFLK</td><td>IGF-1 receptor; SEQ ID NO:5</td></tr>
<tr><td>ERETQIAKGNEQSFRVDLRTLLR</td><td>MHC; SEQ ID NO:1</td></tr>
<tr><td>.:|..|..:.|::::| . :.</td><td>47% similar</td></tr>
<tr><td>KKENKIVPSKEIVWWMNLAEKIP</td><td>Leptin receptor; SEQ ID NO:6</td></tr>
<tr><td>ERETQIAKGNEQSFRV DLRTLLRYY</td><td>MHC: SEQ ID NO:1</td></tr>
<tr><td>| | |. ..|| .::: | | :. |</td><td>48% similar</td></tr>
<tr><td>BYELQYKEVNETKWKMMDPILTTSVPVY</td><td>growth hormone receptor; SEQ ID NO:12</td></tr>
<tr><td>ERETQIAKGNEQSFRVDLRTLLRYY</td><td>MHC; SEQ ID NO:1</td></tr>
<tr><td>|:.. .::: | .:|.||:. |</td><td>48% similar</td></tr>
<tr><td>EKKPVPWESHNSSETCGLPTLVQTY</td><td>G-CSF receptor; SEQ ID NO:7</td></tr>
<tr><td>ERETQIAKG NEQSFRVDLRTLLR</td><td>MHC; SEQ ID NO:1</td></tr>
<tr><td>:|. . . .|| . |</td><td>42% similar</td></tr>
<tr><td>YKEGTMLNCECKTGFRRIKSGSLY</td><td>IL-2 receptor; SEQ ID NO:8</td></tr>
</table>

TABLE 1-continued

Sequence similarities

```
ERETQIAKGNEQS FRVDLRTLLR      MHB; SEQ ID NO:1
 |.  . | |            |       48% similar
LLEGEPREFVECSECIQCHPECLP      EGF receptor; SEQ ID NO:9
```

Example 2

Methods

Insulin Receptor modification and expression. The human insulin receptor gene, as described in the database references and in Ebina et al. (1985) *Cell* 40:747–758) with a pCR3 expression vector (Invitrogen, catalog no. K3000-01) was transfected by electroporation into HeLa cells. Methods of electroporation are described in Boggs et al. (1986) *Ex. Hematol.* 149:988–994. In the transfected cells the receptors show insulin dependent internalization.

A mutated form of the insulin receptor was created by deleting residues 713 to 740 (SEQ ID No:10; PKTDSQILKELEESSFRKTFEDYLHNV) using amplification primers that spanned the region to be deleted. The deletion mutant, mIR, was transfected into HeLa cells and internalization of the mIR was then tested.

Measurement of IR Internalization

Receptor internalization was performed essentially as described in Stagsted et al. (1990) *Cell* 62:297–307. Briefly, 50 μl of the transfected cells at 106 cells/ml were incubated in a shaking water bath at 37° C. with 625 pM 1251-labeled insulin in the absence or presence of 10 μM of peptide as shown in Table 1, and the final volume brought to 100 μl. The cells were then diluted with 50 μl of KRHB (pH7.2) (no acid wash) or 50 μl of KRHB (pH 2.0) (acid wash) and incubated on ice for 5 min. The cells were finally harvested by centrifugation on top of silicone oil, and both free and cell-associated radioactivity was measured.

Glucose Transport in Adipose Cells

The biological activity of the peptides were measured by their effect on glucose uptake in rat adipose cells as described (Stagsted et al. (1991) *J. Biol. Chem.* 266:12844–12847). Briefly, rat adipose cells were obtained from epididymal fat pads and suspended in Krebs-Ringer HEPES buffer (KRH) with 5% bovine serum albumin at a lipocrit of 10% (final). The peptide effect was measured in cells maximally stimulated with insulin (10 nM). After equilibration at 37° C. for 30 min the cells were incubated for 30 min at 37° C. with buffer (basal), 10 nM insulin plus peptide. ⁻C-D-glucose was added, and the cells were incubated for an additional 30 min and harvested on oil. Biological activity was measured by a dose-response curve to interpolate the $EC_{50}$ value, taking the maximum enhancement of insulin effect (about 40% over the insulin-only maximum) as 100%. Most of the peptides were not tested at higher concentrations than 30 μM. Peptides that enhanced the maximum insulin effect by less than 20% at 30 μM were considered inactive.

Peptides

The peptides were assembled stepwise either on a phenylacetamidomethyl (PAM) resin using the t-Boc NMP/ HOBt protocol of an Applied Biosystems Model 430A peptide synthesizer, or on a p-alkoxy benzyl alcohol (Wang) resin using a modified Fmoc/BOP protocol of a Milligen/ Biosearch Model 9600 synthesizer. The desired peptides were confiumed by sequence analysis, amino acid composition, and fast atom bombardment mass spectrometry. The peptides were activated by incubation of 1 mM stock solution at 37° C. in 0.1 M NaCl overnight (Stagsted et al. (1991) *J. Biol. Chem.* 266:12844–12847).

Results

Effect of peptides on receptor internalization. The kinetics of internalization for insulin receptor and mutated insulin receptor were determined in the absence or presence of the peptides: SEQ ID No:3, KTDSQILKELEESSFRKT-FEDYLH (pepIR) and SEQ ID No:11, GNEQSFRVDL-RTLLRYAGGGNEQSFRVDLRTLLRYA (DS-A85). The data are shown in Table 2, where the numbers indicate percent internalized receptor.

TABLE 2

| Time (min) | IR | mIR | IR + DS-A85 | mIR + DS-A85 | IR + PEPIr | MIR + pepIR |
|---|---|---|---|---|---|---|
| 5 | 6 ± 4 | 4 ± 5 | 5 ± 4 | −1 ± 5 | 6 ± 4 | 5 ± 4 |
| 15 | 39 ± 7 | 2 ± 2 | 9 ± 6 | 0 ± 3 | 2 ± 2 | −2 ± 1 |
| 30 | 68 ± 6 | 4 ± 5 | 14 ± 6 | 2 ± 3 | 6 ± 4 | 0 ± 2 |
| 60 | 74 ± 8 | 5 ± 4 | 17 ± 3 | 1 ± 4 | 2 ± 4 | 2 ± 3 |

The data show that the mutated insulin receptor mIR does not internalize upon insulin binding, whereas more than 50% of the wild type IR is internalized within 30 minutes. The pepIR peptide inhibits receptor internalization to the same extent as DS-A85.

Effect of peptides on glucose uptake. At maximal insulin stimulation, the addition of pep1R did not significantly affect glucose uptake, indicating that pepIR does not affect GLUT4 internalization. Glucose uptake is enhanced 14±3 fold by the addition of 10 μM insulin. Insulin+10 μM of the DS-A85 peptide enhances glucose uptake 22±4 fold, whereas addition of insulin+10 μM pepIR enhances glucose uptake 12±4 fold, a result not significantly different from insulin alone.

The GLUT4pep (SEQ ID No:2), at a concentration of 10 μM, does not affect insulin receptor internalization by the transfected cells. In the presence of peptide the per cent internalized receptor is 6±9, in the absence of peptide it is 64±7. The peptide does inhibit the internalization of GLUT4, as shown by the effect on glucose uptake at maximal insulin stimulation. In the presence of 10 nM insulin, the enhancement of glucose uptake was 12±4 fold. The enhancement was increased to 24±2 fold with the addition of the GLUT4pep. The peptide therefore seems to inhibit internalization of GLUT4, but not insulin receptor.

It is evident from the above results that oligopeptides having the sequence of the extracellular domain of a cell surface receptor, and having sequence identity with a region of an MHC class I antigen, are effective in inhibiting the internalization of the corresponding receptor. The peptides are therapeutically useful in enhancing the cellular response to hormones such as insulin.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for screening for a candidate agent capable of modulating internalization of a cell surface receptor after binding to its corresponding ligand, said method comprising:
    a) combining in a first sample said candidate agent with a cell comprising a modified cell surface receptor and ligand for said modified cell surface receptor, wherein said modification is only at an external sequence regulating internalization of said cell surface receptor and results in a modification of internalization of said cell surface receptor after binding to its corresponding ligand;
    b) combining in a second sample said candidate agent with a cell comprising the wild type cell surface receptor and ligand for said cell surface receptor;
    c) determining the binding of said candidate agent to said cells, wherein a difference in binding in a) and b) indicates that said agent is capable of modulating internalization of said cell surface receptor.

2. A method according to claim 1, wherein said cell surface receptor regulates glucose metabolism.

3. A method according to claim 1, wherein said cell surface receptor binds to a growth factor.

4. A method according to claim 1, wherein said cell surface receptor regulates lipid metabolism.

5. A method according to claim 1, wherein said cell surface receptor is from human cells and is selected from the group consisting of the insulin receptor, glucose transporter, leptin receptor, LDL receptor, insulin like growth factor receptor, granulocyte colony stimulating factor receptor, interleukin 2 receptor, growth factor and epidermal growth factor.

6. A method according to 5, wherein said sequence is SEQ ID NO:3,2,6,4,5,7,8,12 or 9, respectively.

7. A method according to claim 6, wherein said sequence is SEQ ID NO:3 and said receptor is the insulin receptor.

8. A method according to claim 6, wherein said sequence is SEQ ID NO:2 and said receptor is the glucose transporter.

9. A method for screening for an agent capable of modulating internalization of a cell surface receptor comprising an external sequence comprising an internalization sequence regulating the internalization of said cell surface receptor, said method comprising:
    combining at least a portion of said cell surface receptor comprising said external sequence with said agent and determining the binding of said agent to said internalization sequence:

whereby binding of said agent to said internalization sequence indicates activity for modulating internalization of said cell surface receptor.

10. A method according to claim 9, wherein said determining is by competitive binding with an oligopeptide comprising at least an 8 and fewer than about 40 amino acid portion of said internalization sequence.

11. A method according to claim 10, wherein at least one of said oligopeptide and said agent is labeled with a detectable label.

12. A method according to claim 10, wherein said sequence is SEQ ID NO: 3 and said receptor is the insulin receptor.

13. A method according to claim 10, wherein said sequence is SEQ ID NO: 2 and said receptor is the glucose transporter.

14. A method according to claim 9, wherein said at least a portion of said cell surface receptor is bound to an insoluble support.

15. A method for screening for an agent capable of modulating internalization of a cell surface receptor comprising an external sequence comprising an internalization sequence regulating the internalization of said cell surface receptor, said method comprising:

combining at least a portion of said cell surface receptor comprising said external sequence with said agent and an oligopeptide comprising from at least 8 to and fewer than about 40 amino acids of said internalization sequence;

determining at least one of the binding of said agent or said oligopeptide to said internalization sequence;

whereby binding of said agent to said internalization sequence or a reduction in binding of said oligopeptide indicates activity for modulating internalization of said cell surface receptor.

16. A method according to claim 15, wherein at least one of said agent or said oligopeptide is labeled.

* * * * *